(12) United States Patent
Yano et al.

(10) Patent No.: US 8,367,000 B2
(45) Date of Patent: Feb. 5, 2013

(54) CASSETTE AND MEASURING APPARATUS

(75) Inventors: Takakazu Yano, Tokyo (JP); Tadahiro Fukuda, Tokyo (JP); Miharu Sugiura, Tokorozawa (JP); Hiroyuki Sato, Fussa (JP)

(73) Assignee: Citizen Holding Co., Ltd., Tokyo (JP)

( * ) Notice: Subject to any disclaimer, the term of this patent is extended or adjusted under 35 U.S.C. 154(b) by 1230 days.

(21) Appl. No.: 12/158,268

(22) PCT Filed: Dec. 21, 2006

(86) PCT No.: PCT/JP2006/326162
§ 371 (c)(1),
(2), (4) Date: Jun. 19, 2008

(87) PCT Pub. No.: WO2007/072990
PCT Pub. Date: Jun. 28, 2007

(65) Prior Publication Data
US 2009/0324448 A1     Dec. 31, 2009

(30) Foreign Application Priority Data

Dec. 21, 2005   (JP) ................................ 2005-367789
Sep. 29, 2006   (JP) ................................ 2006-268525

(51) Int. Cl.
*G01N 33/00*     (2006.01)
(52) U.S. Cl. ..................... 422/82.05; 422/500; 422/504; 422/560; 422/561
(58) Field of Classification Search ............... 422/82.05, 422/500, 504, 560, 561
See application file for complete search history.

(56) References Cited

U.S. PATENT DOCUMENTS 5,096,669 A  *  3/1992  Lauks et al. ............. 204/403.02
7,419,821 B2 *  9/2008  Davis et al. ................ 435/288.5

FOREIGN PATENT DOCUMENTS

| JP | H09-080037 A | 3/1997 |
| JP | H11-271259 A | 10/1999 |
| JP | 2000-081386 A | 3/2000 |
| JP | 2002-098628 | 4/2002 |
| JP | 2005-121655 | 5/2005 |
| JP | 2002-320592 | 11/2005 |
| WO | WO 2005/093410 A1 | 10/2005 |

OTHER PUBLICATIONS

International Search Report from Japanese Patent Office.

* cited by examiner

*Primary Examiner* — Sam P Siefke
(74) *Attorney, Agent, or Firm* — Finnegan, Henderson, Farabow, Garrett & Dunner, L.L.P.

(57) ABSTRACT

An object of the invention is to provide a cassette and a measuring apparatus that can filter a sample for the optical measurement of an optically active substance and clean a sample flow channel by using a simple configuration. More specifically, the invention is directed to a cassette which includes a filter for filtering out a measurement interfering component from a sample, a container containing the filter, a cleaning liquid or cleaning agent for cleaning a sample flow channel, and a storage tank for storing the cleaning liquid or cleaning agent, and to a measuring apparatus having such a cassette.

10 Claims, 15 Drawing Sheets

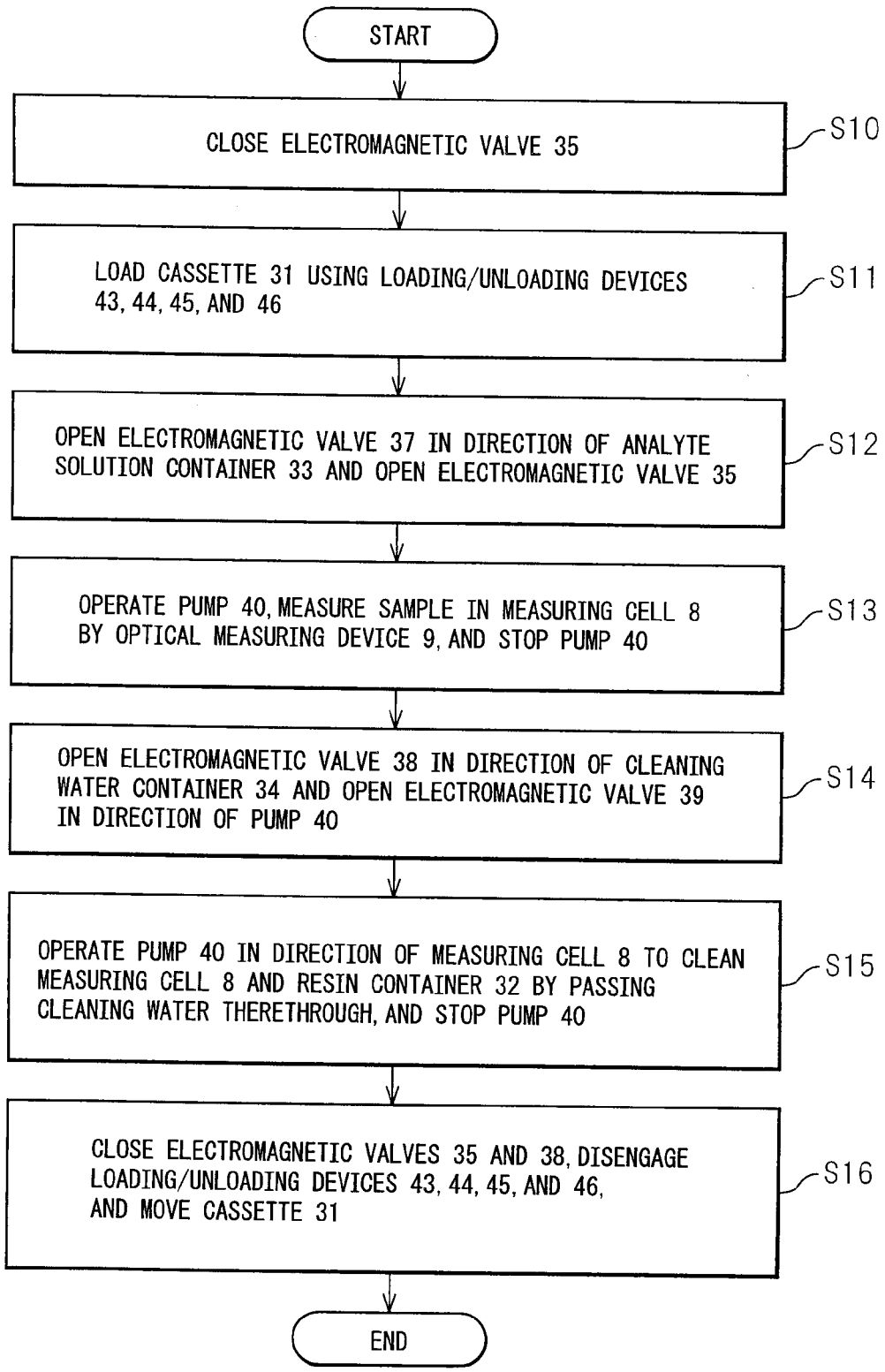

CASSETTE AND MEASURING APPARATUS

FIELD OF THE INVENTION

The present invention relates to a cassette for filtering a sample and a measuring apparatus having such a cassette, and more specifically to a cassette for filtering out interfering substances that can interfere with the optical measurement of an optically active substance and a measuring apparatus having such a cassette.

BACKGROUND OF THE INVENTION

It is known that measuring the levels of urinary components is useful for health management. In particular, quantitative measurement of glucose concentration in urine is important as it provides a criterion to diagnose diabetes which is increasing year by year. A method for measuring glucose concentration in urine, i.e., urine sugar concentration, is known in the art which uses an enzyme-based biosensor in accordance with a glucose oxidase (GOP) method (refer, for example, to patent document 1).

In this method, when urine is brought into contact with an enzyme membrane formed by immobilizing GOP onto an electrode coated with a selective permeable membrane, the reactions shown by the following equations (1) and (2) take place, and the glucose concentration is obtained by measuring the amount of the electric current that flows.

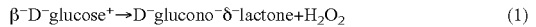
$$\beta\text{-D-glucose}^+ \rightarrow \text{D-glucono-}\delta\text{-lactone} + H_2O_2 \quad (1)$$

$$H_2O_2 \rightarrow 2H^+ + O_2 + 2e^- \quad (2)$$

A method is also known that measures the concentration of urine sugar by an optical method utilizing the optical activity of the urine sugar (refer, for example, to patent document 2). According to this method, since the measurement can be performed without directly contacting the urine, contaminants do not adhere to sensors, and the measuring system can be used for an extended period of time without requiring replacement of parts or consumables.

The method of measuring the concentration of an optically active substance in urine, utilizing the optical activity, is based on the following equation (3).

$$\theta = \frac{1}{100} \times [\alpha] \lambda T \times c \times L \quad (3)$$

θ is the angle of rotation due to optical activity, and generally, rotation to the right is taken as + and rotation to the left as −. $[\alpha]\lambda T$ is the specific rotation of the optically active substance when the wavelength of light is λ and the temperature T, and is a constant unique to the substance causing the rotation. Further, c is the concentration of the optically active substance in the urine, and L is the optical path length of the sample (urine). In equation (3), since the specific rotation $[\alpha]\lambda T$, the wavelength λ, the temperature T, and the optical path length L are known, the concentration c can be obtained by measuring the angle of optical rotation θ.

However, urine contains many components other than the component to be measured. For example, in addition to the urine sugar (urine glucose) to be measured, urine contains interfering components such as vitamin C (ascorbic acid), peptides, amino acids, etc., excreted after taking nutritional supplements, etc. Vitamin C has a strong reducing power and affects the electric current used in the enzyme-based measurement; furthermore, since it is an optically active substance (specific rotation: 23°), it also affects the optical measurement utilizing the optical activity. Such interfering components not only contribute to degrading the accuracy of the measurement, but can contaminate the measuring parts.

In view of this, it is known to perform measurement after removing such interfering components (refer, for example, to patent document 3). For example, when measuring urine sugar, vitamin C and amino acids are removed using an ion-exchange resin, and peptides are removed using a synthetic adsorbent resin or activated carbon.

However, if a filtering mechanism containing such an ion-exchange resin, synthetic adsorbent resin, activated carbon, etc. is used continuously, part of the previously measured urine remains in the filtering mechanism itself, resulting in an inability to make an accurate measurement. One possible method to address this problem would be to clean the filtering mechanism with clean water or a cleaning liquid after use, but adding a cleaning mechanism would require installing a special cleaning container, leading to such problems as increasing the size and cost of the measuring apparatus while, at the same time, increasing the complexity of maintenance work.

However, the structure of a cassette for continuous measurement, including a specific flow channel design, has not been disclosed in the prior art. There has also been no disclosure of a specific cassette structure that addresses hygienic concerns, for example, by making provisions to prevent the hand from contacting liquids such as urine when removing the cassette.

It is known to clean the urine flow channel after measuring the urine, as described above, but in some cases, cleaning it with clean water may not be sufficient. In particular, to prevent growth of fungi, a special cleaning liquid may become necessary in addition to using clean water. In view of this, it is known to use ionized water generated by electrolyzing tap water (refer, for example, to patent document 4).

It is also known to provide an analyzing apparatus that uses analytical reagents instead of cleaning liquids (refer, for example, to patent document 5). This analyzing apparatus is designed to make optical measurements by using a single separation column (filled with resin) and a plurality of reagents for analyzing various kinds of amino acids.

However, storing large quantities of antiseptics, cleaning agents, or reagents in advance within the apparatus has involved problems in terms of space and maintenance. Furthermore, storing various kinds of cleaning liquids, etc. for various kinds of analytes in advance within the apparatus has also involved problems in terms of space and maintenance.

[Patent document 1] Japanese Unexamined Publication No. H11-271259 (FIG. 2)
[Patent document 2] Japanese Unexamined Publication No. 2000-81386 (FIG. 1)
[Patent document 3] International Publication WO 2005/093410 Pamphlet (FIG. 1)
[Patent document 4] Japanese Unexamined Publication No. 2002-98628 (FIG. 2)
[Patent document 5] Japanese Unexamined Publication No. H09-80037 (FIG. 3)

SUMMARY OF THE INVENTION

Accordingly, it is an object of the present invention to provide a cassette and a measuring apparatus that can solve the above deficiencies.

It is another object of the present invention to provide a cassette and a measuring apparatus that can filter a sample for the optical measurement of an optically active substance and clean a sample flow channel by using a simple configuration.

It is another object of the present invention to provide a cassette and a measuring apparatus that can be repeatedly used for filtering a sample for the optical measurement of an optically active substance.

It is another object of the present invention to provide a cassette and a measuring apparatus that can save space and maintenance work and can achieve powerful cleaning and extensive measurements.

A cassette according to the present invention includes a filter for filtering out a measurement interfering component from a sample, a container containing the filter; a cleaning liquid or cleaning agent for cleaning a sample flow channel, and a storage tank for storing the cleaning liquid or cleaning agent.

A cassette according to the present invention includes a filter for filtering out a measurement interfering component from a sample, a container containing the filter, the container having a first inlet port through which the sample is introduced from outside the cassette and a first outlet port through which the sample passed through the filter exits, a discharge drain having a second inlet port through which the sample passed through the filter is introduced and a second outlet port through which the sample introduced through the second inlet port is discharged outside the cassette, a transferring member for transferring the sample exiting from the first outlet port of the container onto the second inlet port of the discharge drain, a cleaning liquid or cleaning agent for cleaning a sample flow channel; and a cleaning liquid storage tank for storing the cleaning liquid, the tank having a third outlet port through which the cleaning liquid is fed out of the cassette.

A cassette according to the present invention includes a filter for filtering out a measurement interfering component from a sample, a cleaning liquid or cleaning agent for cleaning a sample flow channel, and a cleaning liquid storage tank for storing the cleaning liquid or cleaning agent.

A cassette according to the present invention includes a plurality of filters each for filtering out a measurement interfering component from a sample, a plurality of inlet ports for introducing the sample into the respective filters from outside the cassette, and a plurality of outlet ports for discharging the sample from the respective filters, wherein the plurality of inlet ports and the plurality of outlet ports are arranged on the same side of the cassette.

A measuring apparatus according to the present invention includes a cassette having a filter for filtering out a measurement interfering component from a sample, a container containing the filter, a cleaning liquid or cleaning agent for cleaning a sample flow channel, and a storage tank for storing the cleaning liquid or cleaning agent, a cassette holder for detachably holding the cassette, a measuring container for holding the sample from which the measurement interfering component has been filtered out by the filter for optical measurement by an optical measuring section; and the optical measuring section for optically measuring an optically active substance contained in the sample in the measuring container.

A measuring apparatus according to the present invention includes a cassette having a filter for filtering out a measurement interfering component from a sample, a container containing the filter, the container having a first inlet port through which the sample is introduced from outside the cassette and a first outlet port through which the sample passed through the filter exits, a discharge drain having a second inlet port through which the sample passed through the filter is introduced and a second outlet port through which the sample introduced through the second inlet port is discharged outside the cassette, a transferring member for transferring the sample exiting from the first outlet port of the container onto the second inlet port of the discharge drain, a cleaning liquid for cleaning a sample flow channel, and a cleaning liquid storage tank for storing the cleaning liquid, the tank having a third outlet port through which the cleaning liquid is fed out of the cassette, and a cassette holder for detachably holding the cassette, the holder having a sample inlet tube for introducing the sample into the first inlet port, a sample outlet tube for discharging the sample from the second outlet port, and a cleaning liquid outlet tube for feeding the cleaning liquid from the third outlet port.

A measuring apparatus according to the present invention is a concentration measuring apparatus for measuring the concentration of a prescribed solution, comprising a measuring means for measuring a characteristic of a prescribed solution component and a loading/unloading means for loading/unloading a prescribed container, wherein a pretreatment container containing a component necessary as a pretreatment for measuring the characteristic of the prescribed solution component is loaded by the loading/unloading means, and a cleaning container containing a component at least necessary for cleaning the measuring means is loaded by the loading/unloading means in such a manner as to be exchangeable for the pretreatment container.

Preferably, the measuring apparatus according to the present invention includes a container group having a plurality of containers exchangeable by the loading/unloading means, wherein the plurality of containers include the pretreatment container and the cleaning container.

Preferably, in the measuring apparatus according to the present invention, the pretreatment container and the cleaning container are simultaneously loaded by the loading/unloading means.

Preferably, in the measuring apparatus according to the present invention, the pretreatment container is cleaned with a solution containing the component contained in the cleaning container.

Preferably, in the measuring apparatus according to the present invention, more than one pretreatment container is simultaneously loaded by the loading/unloading means.

Preferably, in the measuring apparatus according to the present invention, each container is formed in a cylindrical shape or in the shape of a polygonal column.

Preferably, in the measuring apparatus according to the present invention, the container group is constructed in a disc shape.

BRIEF DESCRIPTION OF THE DRAWINGS

FIG. 4 is a diagram showing a system flowchart of a control device 36 shown in FIG. 1.

DETAILED DESCRIPTION OF THE PREFERRED EMBODIMENT

A cassette and a measuring apparatus according to the present invention will be described below with reference to the drawings.

A first embodiment of the present invention will be described below with reference to FIGS. 1 to 4.

Figure 1:
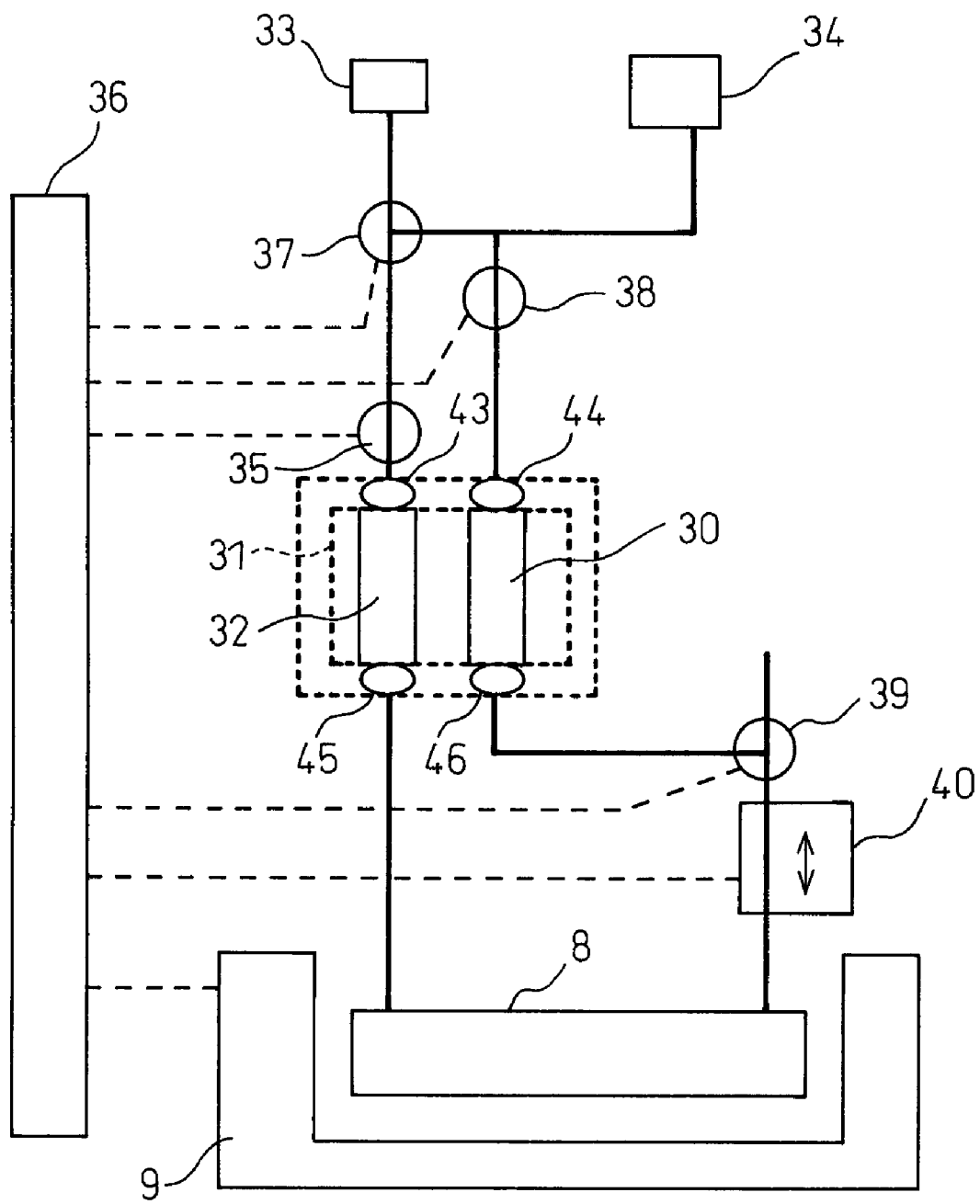
FIG. 1 is a schematic diagram showing the overall system configuration of a measuring apparatus according to a first embodiment.

FIG. 1 is a schematic diagram showing the overall system configuration of a measuring apparatus according to the first embodiment.

In the figure, a control device 36 comprises a CPU for controlling the entire system, and its peripheral circuitry. An optical measuring device 9 is a device for measuring the angle of optical rotation produced by an analyte solution (urine) held in a measuring cell 8, and performs the measurement under instruction from the control device 36. A cleaning water container 34 is a container for storing a cleaning liquid, and an analyte solution container 33 is a container for holding the analyte solution (urine) to be measured. An electromagnetic valve 37 has the function of connecting a resin container 32 to either the cleaning water container 34 or the analyte solution container 33, whichever is selected, under instruction from the control device 36. An electromagnetic valve 35 has the function of opening or closing the passage connecting between the electromagnetic valve 37 and the measuring cell 8, under instruction from the control device 36. An electromagnetic valve 38 has the function of opening or closing the side leading to the cleaning water container 34, under instruction from the control device 36. An electromagnetic valve 39 has the function of connecting the outlet of a pump 40 to either the discard side or the side leading to a cleaning container 30, whichever is selected, under instruction from the control device 36.

A loading/unloading device 43 is a device for loading/unloading a cassette 31 under instruction from the control device 36, and has the function of loading/unloading the resin container 32 and the cleaning container 30 at the same time. The cassette 31 is formed from polyvinyl chloride. The cassette 31 accommodates a plurality of container pairs each comprising a resin container 32 containing resins (ion-exchange resin and synthetic adsorbent resin) for removing interfering components and a cleaning container 30 containing antiseptics. The resin container 32 and the cleaning container 30 are each provided with liquid feed holes at the inlet and outlet sides, and a membrane filter for preventing the passage of the content is provided at the outlet side. The cassette 31 accommodates a plurality of containers for a plurality of measurement cycles, and is constructed so that the containers can be continuously and automatically changed.

The optical measuring device 9 is a device for measuring the angle of optical rotation produced by the analyte solution (urine) held in the measuring cell 8, and performs the measurement under instruction from the control device 36. The pump 40 delivers the liquid between the electromagnetic valve 39 and the measuring cell 8 or stops delivering the liquid between them, under instruction from the control device 36.

Next, a changing system for the cassette 31 will be described in detail.

Figure 2:
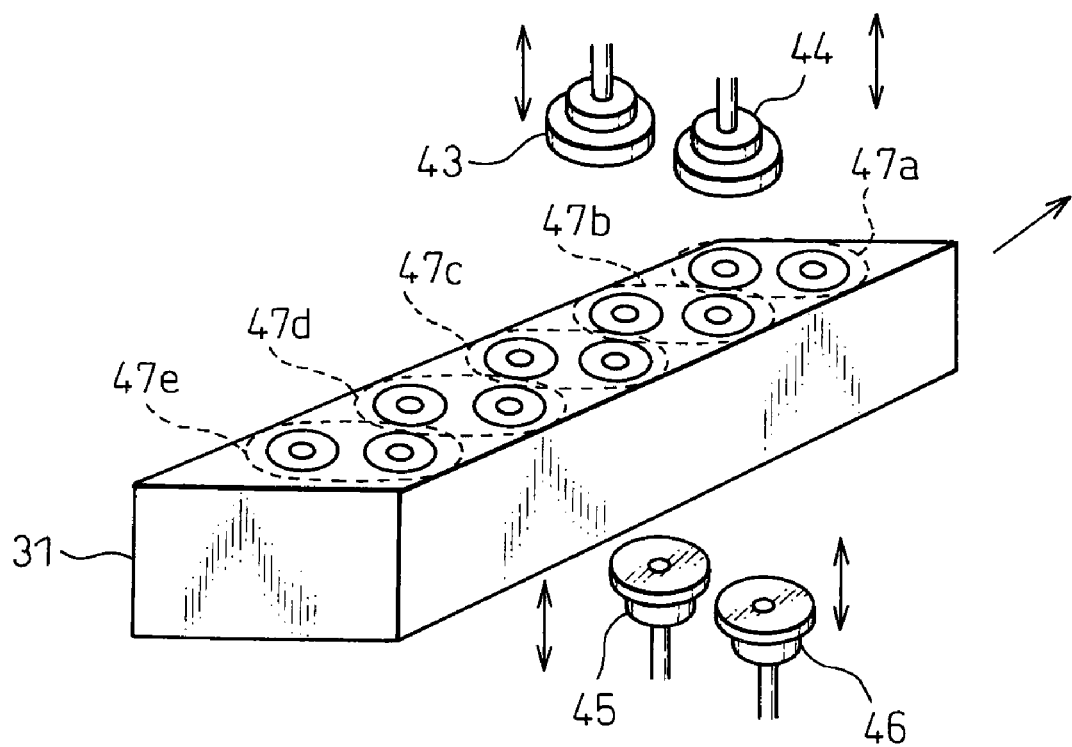
FIG. 2 is a diagram showing the details of an automatic continuous changing mechanism for a cassette 31.

FIG. 2 is a diagram showing the details of the automatic continuous changing mechanism for the cassette 31. In the figure, the loading/unloading devices 43 and 44 move upward when unloading the containers and downward when loading the containers. On the other hand, the loading/unloading devices 45 and 46 move downward when unloading the containers and upward when loading the containers.

When changing the containers loaded in the cassette 31, first the loading/unloading devices 43 and 44 move upward and the loading/unloading devices 45 and 46 downward, and after that, the cassette 31 moves in the direction shown by arrow in the figure by a prescribed length until the container group 47b comes to the designated position. Then, the loading/unloading devices 43 and 44 move downward and the loading/unloading devices 45 and 46 upward, thus holding the cassette 31 fixed in position.

With the above operation, the containers loaded in the cassette 31 are automatically changed. The container groups 47a, 47b, 47c, 47d, and 47e each comprise a pair of containers, one being a resin container containing resins and the other being a cleaning container containing antiseptics.

The figure here shows the condition in which the container group 47a is already used and the container group 47b is being positioned for use. In other words, the measurement and cleaning is about to be performed using the container group 47b. After that, the container groups 47c, 47d, and 47e are used one after another in the order named.

Figure 3A:
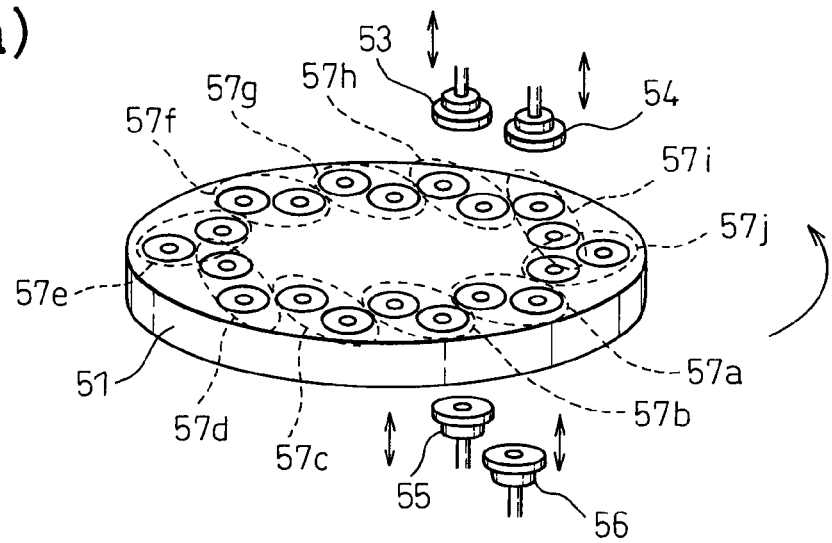
FIG. 3(a) is a diagram showing another example in which the cassette is constructed in a disc shape.

FIG. 3 is a diagram showing another example in which the cassette is constructed in a disc shape. In FIG. 3(a), the loading/unloading devices 53 and 54 move upward when unloading the containers and downward when loading the containers. On the other hand, the loading/unloading devices 55 and 56 move downward when unloading the containers and upward when loading the containers.

When changing the containers loaded in the cassette 51, first the loading/unloading devices 53 and 54 move upward and the loading/unloading devices 55 and 56 downward, and after that, the cassette 31 rotates in the direction shown by arrow in the figure by a prescribed amount until the container group 57b comes to the designated position. Then, the loading/unloading devices 53 and 54 move downward and the loading/unloading devices 55 and 56 upward, thus holding the cassette 51 fixed in position.

With the above operation, the containers loaded in the cassette 51 are automatically changed. Here, the container groups 57a, 57b, 57c, 57d, 57e, 57f, 57g, 57h, 57i, and 57j each comprise a pair of containers, one being a resin container containing resins and the other being a cleaning container containing antiseptics.

The FIG. 3(a) shows the condition in which the container group 47a is already used and the container group 47b is being positioned for use. In other words, the measurement and cleaning is about to be performed using the container group 47b. After that, the container groups 47c, 47d, and 47e are used one after another in the order named.

Figure 3B:
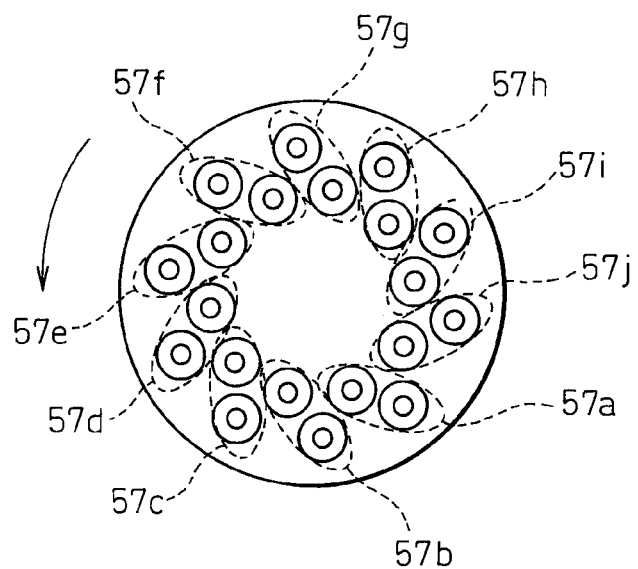
FIG. 3(b) is a plan view of FIG. 3(a).

FIG. 3(b) is a top plan view of the cassette 51. As shown, the containers containing resins are arranged around the outside of the disc, while the containers containing antiseptics are arranged around the inside. The inside containers are arranged alternately between the outside containers so as to reduce the overall size of the disc-shaped cassette 51.

FIG. 4 is a diagram showing a system flowchart of the control device 36 shown in FIG. 1.

First, the electromagnetic valve 35 is closed to stop the solution flow (S10).

Next, the cassette 31 is loaded using the loading/unloading devices 43, 44, 45, and 46 (S11).

Next, the electromagnetic valve 37 is opened in the direction of the analyte solution container 33, and the electromagnetic valve 35 is also opened, thus securing a path for feeding the analyte solution (urine) to the cassette (S12).

Next, the pump 40 is operated in the direction of the electromagnetic valve 39, causing the analyte solution (urine) to pass through the resin container 32 and flow into the measuring cell 8 for measurement by the optical measuring device 9; after the measurement is done, the pump 40 is stopped (S13).

Next, the electromagnetic valve 38 is opened in the direction of the cleaning water container 34, and the electromagnetic valve 39 is opened in the direction of the pump 40 (S14).

Next, the pump 40 is operated in the direction of the measuring cell 8, causing the cleaning water from the cleaning water container 34 to pass through the measuring cell 8 and the resin container 32, thus cleaning the entire system (S15). During this process, the antiseptics contained in the cleaning container 30 are dissolved into the cleaning liquid which thus serves to inhibit the growth of fungi. In other words, growth of fungi can be prevented without having to use a special cleaning liquid but by using only the cleaning water.

Finally, the electromagnetic valves 35 and 38 are closed, the loading/unloading devices 43, 44, 45, and 46 are disengaged, and the cassette 31 is moved (16).

In the first embodiment of the present invention, the substance to be contained in the cleaning container is not limited to antiseptics, but instead, a cleaning agent or a chemical or like substance effective for cleaning may be contained therein. Further, the number of containers in each container group is not limited to two, but each container group may consist of three or more containers, the only requirement being that a plurality of containers be used.

Figure 5:
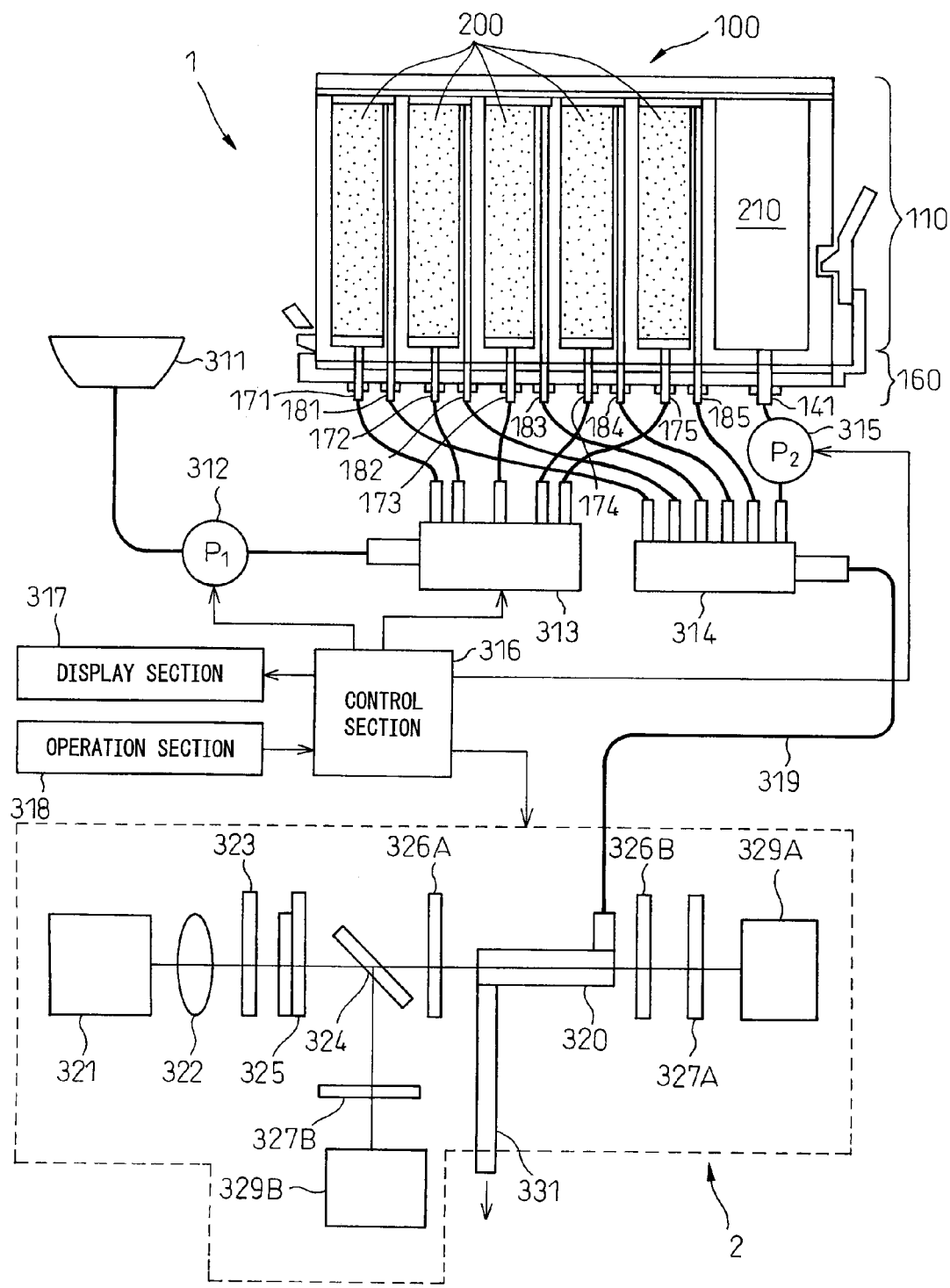
FIG. 5 is a diagram schematically showing a specific configuration example.

A specific configuration example according to the first embodiment will be described below with reference to FIGS. 5 to 10. FIG. 5 is a diagram schematically showing the specific configuration example.

The measuring apparatus 1 comprises a urine collecting section 311, a first pump 312, a flow channel switching section 313, a joint section 314, a second pump 315, a control section 316, a display section 317, an operation section 318, a feed tube 319, a cassette section 100, and an optical measuring section 2.

The cassette section 100 comprises a cassette 110 and a cassette holder 160 for detachably holding the cassette 110, as will be described later. The cassette 110 contains 10 filters 200 and a cleaning liquid 210. The cassette holder 160 has 10 urine inlet tubes 171 to 180 (of which the inlet tubes 171 to 175 are shown here) connected to the respective filters 200 in the cassette 110, 10 urine outlet tubes 181 to 190 (of which the outlet tubes 181 to 185 are shown here) connected to the respective filters 200, and a cleaning liquid outlet tube 141 connected to a cleaning liquid tank which contains the cleaning liquid 210. Since each filter 200 is used only once, the cassette 110 can be used for filtering a total of 10 times. Accordingly, after the cassette 110 has been used 10 times for filtering, the used cassette 110 is removed from the cassette holder 160, and a new cassette is installed. The details of the cassette section 100 will be described later.

The flow channel switching section 313 is connected to all the urine inlet tubes 171 to 180 of the cassette section 100, and is designed so that a selected one of the urine inlet tubes can be connected to the first pump 312 by moving a built-in flow channel switching member in accordance with a control signal from the control section 316.

The joint section 314 is connected to all the urine outlet tubes 181 to 190 of the cassette section 100 and also to the second pump 315. Further, the joint section 314 is connected via the feed tube 319 to a measuring container 320 in the optical measuring section 2. The measuring container 320 is connected to a conduit tube 331.

The control section 316 comprises a CPU, a ROM, a RAM, etc., and in response to an operation entered from the operation section 318, the control section 316 performs processing for the filtering of the urine sampled from the urine collecting section 311 and the optical measurement of the filtered urine to detect urine sugar concentration, by sequentially controlling the optical measuring section 2, the first and second pumps 312 and 315, the flow channel switching section 313, the display section 317, etc., in accordance with programs stored in the ROM, etc.

The particle-type filters 200 accommodated in the cassette 110 are each filled with a mixture comprising an ion-exchange resin for removing ionic components such as vitamin C contained in the urine, a synthetic adsorbent resin for removing peptides, amino acids, etc., contained in the urine, and activated carbon. The fill material of the filters 200 is not limited to this particular mixture, but the mixture may comprise suitable ones selected from among the ion-exchange resin, synthetic adsorbent resin, and activated carbon.

The optical measuring section 2 includes, in addition to the measuring container 320 for storing the urine to be measured, a laser diode 321, a lens 322, a polarizer 323, a liquid crystal device 325, a beam splitter 324, $\lambda/4$ plates 326A and 326B, analyzers 327A and 327B, and photodetectors 329A and 329B. The liquid crystal device 325 is a homogeneously aligned liquid crystal device 325 in which the long axes of the liquid crystal molecules are aligned in the horizontal or vertical direction and, when a voltage is applied, the liquid crystal molecules stand up, and the refractive index in the molecular long axis direction changes, i.e., the liquid crystal device is constructed to function as a phase modulator.

Next, a description will be given of the filtering of the urine and the measurement of the concentration of the optically active substance (urine sugar) contained in the urine.

Upon receiving a measurement start instruction signal entered by the user from the operation section 318, the control section 316 initiates the process for the filtering of the urine and the measurement of the concentration of the optically active substance.

Prior to filtering, the control section 316 controls the flow channel switching section 313 so that the urine inlet tube connected to one of the unused filters 200 in the cassette 110 is connected to the first pump 312.

Next, the control section 316 drives the first pump 312 so that the urine collected in the urine collecting section 311 is introduced into the unused filter 200 selected by the flow channel switching section 313. The urine introduced into the filter 200 from the bottom thereof through one of the urine inlet tubes 171 to 180 in the cassette section 100 by the action of the first pump 312 is passed through the filter 200 where components other than the urine sugar, i.e., vitamin C (ascorbic acid), peptides, amino acids, etc., are removed. The thus filtered urine passes through an associated one of the urine outlet tubes 181 to 190 in the cassette section 100 and flows into the joint section 314, from which the urine is fed into the measuring container 320 through the feed tube 319. For example, the measurement is made in the measuring container 320 while flowing the filtered urine therethrough. The measurement start and end timings are controlled by the control section 316.

In the optical measuring section 2, a beam of light emitted from the laser diode 321 is collimated by the lens 322 into a parallel beam of light. The parallel beam of light is converted by the polarizer 323 into linearly polarized light vibrating in the vertical direction. The linearly polarized light passed through the polarizer 323 enters the liquid crystal device 331. The light passed through the liquid crystal device 331 is split by the beam splitter 324 into reflected light and rectilinearly propagating light. The rectilinearly propagating light enters the λ/4 plate 326A where the light is converted to linearly polarized light. At this time, since the polarization direction of the linearly polarized light depends on the ellipticity of the light passed through the liquid crystal device 331, the polarization direction varies depending on the voltage applied to the liquid crystal device 331. In this way, the polarization direction of the linearly polarized light can be modulated by the liquid crystal device 331. When the linearly polarized light whose polarization direction is thus modulated enters the urine fed into the measuring container 320, the polarization direction is rotated by an unknown amount in accordance with the optical activity of the optically active substance (urine sugar) contained in the urine. The light passed through the urine enters the λ/4 plate 326B where it is converted back to elliptically polarized light, and the elliptically polarized light enters the analyzer 327A. Of the components of the incident light, only the component vibrating in the same direction as the transmission axis of the analyzer 327A is passed through the analyzer 327A. The light passed through the analyzer 327A falls on the photodetector 329A where the light is converted into an electrical signal.

The reflected light separated by the beam splitter 324 is not directed toward the urine but is directed to the analyzer 327B. The light passed through the analyzer 327B falls on the photodetector 329B where the light is converted into an electrical signal.

The difference between the output signal of the photodetector 329A and the output signal of the photodetector 329B corresponds to the difference between the elliptically polarized light before entering the analyzer 327A and the elliptically polarized light before entering the analyzer 327B (that is, the angle of optical rotation through the urine). Accordingly, the control section 316 can determine the angle of optical rotation produced by the optical active substance (urine sugar) in the urine from the difference between the output signal of the photodetector 329A and the output signal of the photodetector 329B. Once the angle of optical rotation produced by the optical active substance (urine sugar) in the urine is determined, the concentration of the optical active substance (urine sugar) in the urine can be obtained using the previously given equation (3), and therefore, the control section 316 can determine the concentration of the optical active substance (urine sugar) in the urine, based on the result of measurement of the angle of optical rotation produced by the optical active substance (urine sugar) in the urine.

The control section 316 can display the concentration of the optical active substance (urine sugar) detected from the urine on the display section 317 and store it in the RAM or the like.

After the measurement is completed, the control section 316 drives the second pump 315 to feed the cleaning liquid 210 into the joint section 314 through the cleaning liquid outlet tube 141. The cleaning liquid 210 further passes through the feed tube 319 and the measuring container 320, and is discharged through the conduit tube 331. As the cleaning liquid 210 passes through the joint section 314, the feed tube 319, and the measuring container 320, the urine and its components adhering to them are washed away, which serves to prevent the growth of fungi and makes it possible to perform the next cycle of measurement with good accuracy. It is to be understood that the cleaning liquid storage tank 142 (see FIG. 2) in each cassette 110 stores the cleaning liquid 210 in an amount sufficient for 10 cycles of cleaning. For the cleaning liquid, use may be made, for example, of a cleaning agent containing a surfactant.

Figure 6:
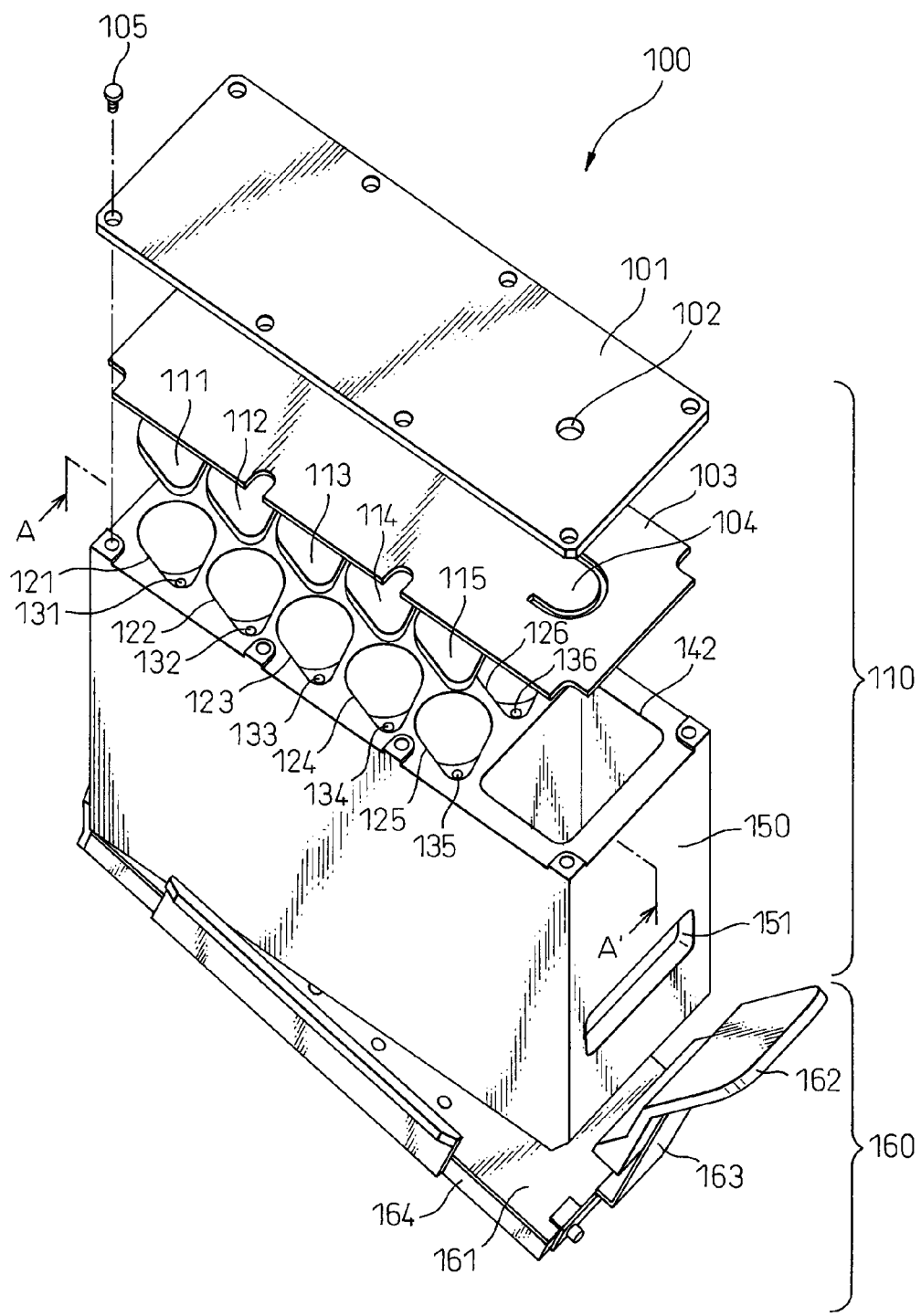
FIG. 6 is an exploded perspective view of a cassette section 100.
Figure 7:
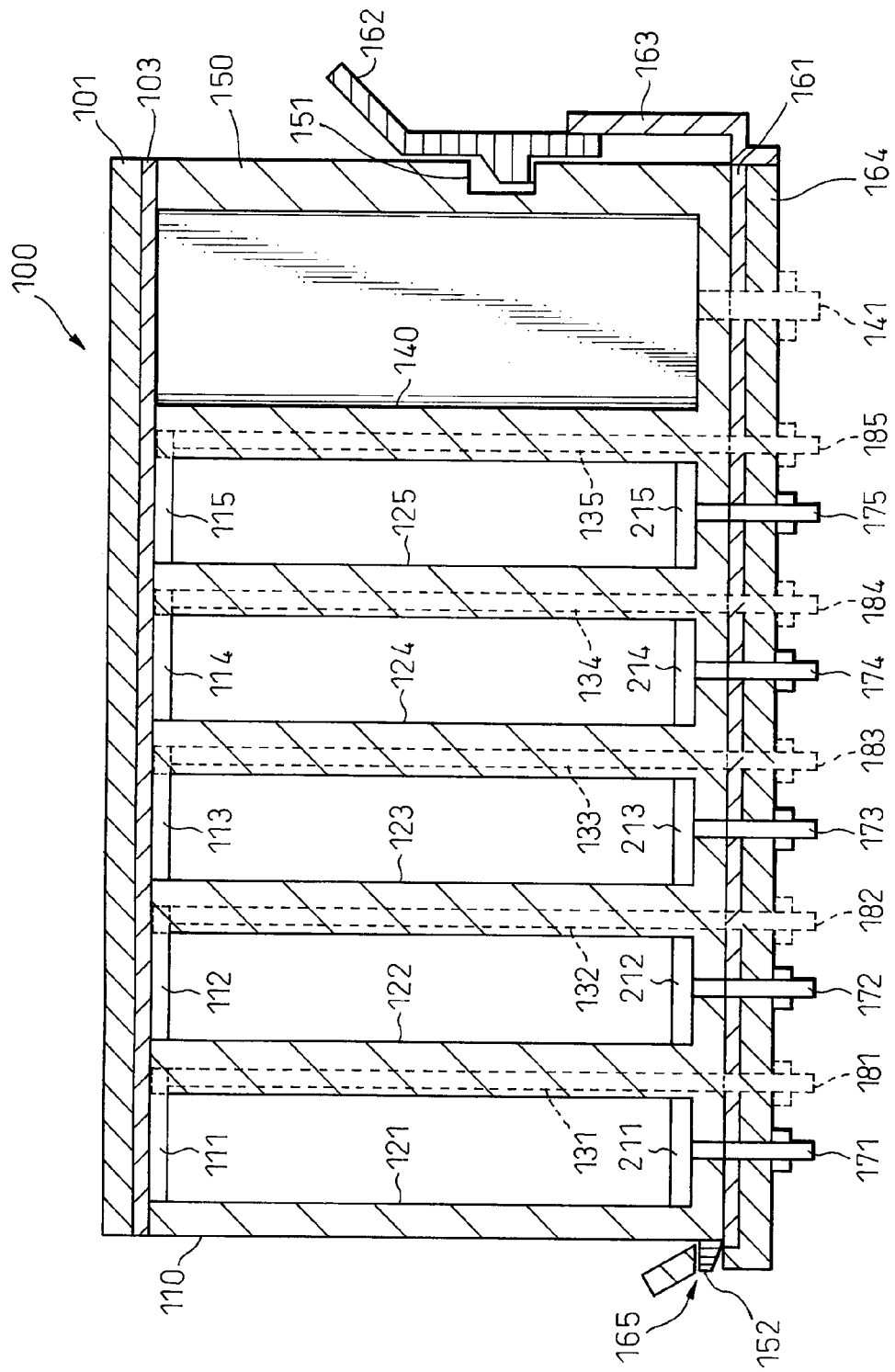
FIG. 7 is a cross-sectional view taken along line AA' in FIG. 6.

FIG. 6 is an exploded perspective view of the cassette section 100, and FIG. 7 is a cross-sectional view taken along line AA' in FIG. 6.

The cassette 110 comprises an upper lid 101 having a hole 102, an upper gasket 103 having a simplified check valve 104, teardrop-shaped upper receiving members 111 to 120, a body 150, and circular lower receiving members 211 to 220. The body 150 includes 10 filter containers 121 to 130 for holding the respective filters 200, discharge drains 131 to 140 for discharging the urine passed through the respective filters, the cleaning liquid tank 142 for storing the cleaning liquid 210, and a recessed portion 151 and protruding portion 152 for fixing the cassette 110 to the cassette holder 160. In FIGS. 6 and 7, only the upper receiving members 111 to 115, filter containers 121 to 126, discharge drains 131 to 136, and lower receiving members 211 to 215 are shown. However, the cassette 110 actually contains 10 filter sets including the upper receiving members, the filter containers, the discharge drains, and the lower receiving members (see FIG. 8).

The cassette holder 160 comprises a lower gasket 161, a securing member 162, a spring member 163, a base 164, a hole 165 formed in the base 164, and side guides 166 and 167, in addition to the urine inlet tubes 171 to 180, urine outlet tubes 181 to 190, and cleaning liquid outlet tube 141.

The upper lid 101 is secured to the body 150 using a plurality of screws 105 by interposing the upper gasket 103 therebetween. The upper gasket 103 is formed from a flexible silicone material, and serves to hermetically seal the upper receiving members 111 to 120 and the cleaning liquid tank 142 when the upper lid 101 is secured to the body 150.

The hole 102 opened in the upper lid 101 serves as an air vent that allows the cleaning liquid 210 to be discharged smoothly from the cleaning liquid tank 142. When the cassette 110 is placed with its upper lid 101 facing up as shown in FIG. 6, the simplified check valve 104 formed in the upper gasket 103 deflects downward along the plane of the figure, permitting air to pass through the hole 102. However, in the event that the cassette 110 is tipped over, for example, the simplified check valve 104 of the upper gasket 103 deflects so as to close the hole 102, thus preventing the cleaning liquid 210 from flowing outside through the hole. The upper gasket 103 also serves the function of preventing the cleaning liquid 210 from vaporizing and escaping through the hole 102. The upper lid itself may be formed with such a simplified check valve and bonded directly to the body 150. In that case, the upper gasket need not be provided.

In installation, the cassette 110 is guided along the side guides 166 and 167 of the cassette holder 160 and, when the protruding portion 152 is engaged in the hole 165 formed in the cassette holder 160, the securing member 162 of the cassette holder 160 is fitted into the recessed portion 151 by the action of the spring member 163, thus securely holding the cassette 110 onto the cassette holder 160.

The lower gasket 161 is formed from a flexible silicone material; when the cassette 110 is secured to the cassette holder 160, the upper gasket 161 is held between the inlet ports 221 to 230 of the filter containers 121 to 130 and the urine inlet tubes 171 to 180 and connects them together in such a manner as to prevent the urine flowing between them from leaking. Likewise, the lower gasket 161 is held between the outlet ports 251 to 260 of the discharge drains 131 to 140 and the urine outlet tubes 181 to 190 and connects them together in such a manner as to prevent the urine flowing between them from leaking. Further, the lower gasket 161 is held between the outlet port 270 of the cleaning liquid tank 142 and the cleaning liquid outlet tube 141 and connects them together in such a manner as to prevent the urine flowing between them from leaking. Here, the upper end of the cleaning liquid outlet tube 141 protrudes above the lower gasket 161, and when the cassette 110 is fixed onto the cassette holder 160, the upper end breaks a seal 271 on the outlet port 270 so that the cleaning liquid 210 can be discharged. The lower gasket is formed, for example, from silicone rubber. In the present embodiment, the lower gasket 161 is provided on the cassette holder 160, but instead, the lower gasket 161 may be provided on the underside of the cassette 110.

Figure 8:
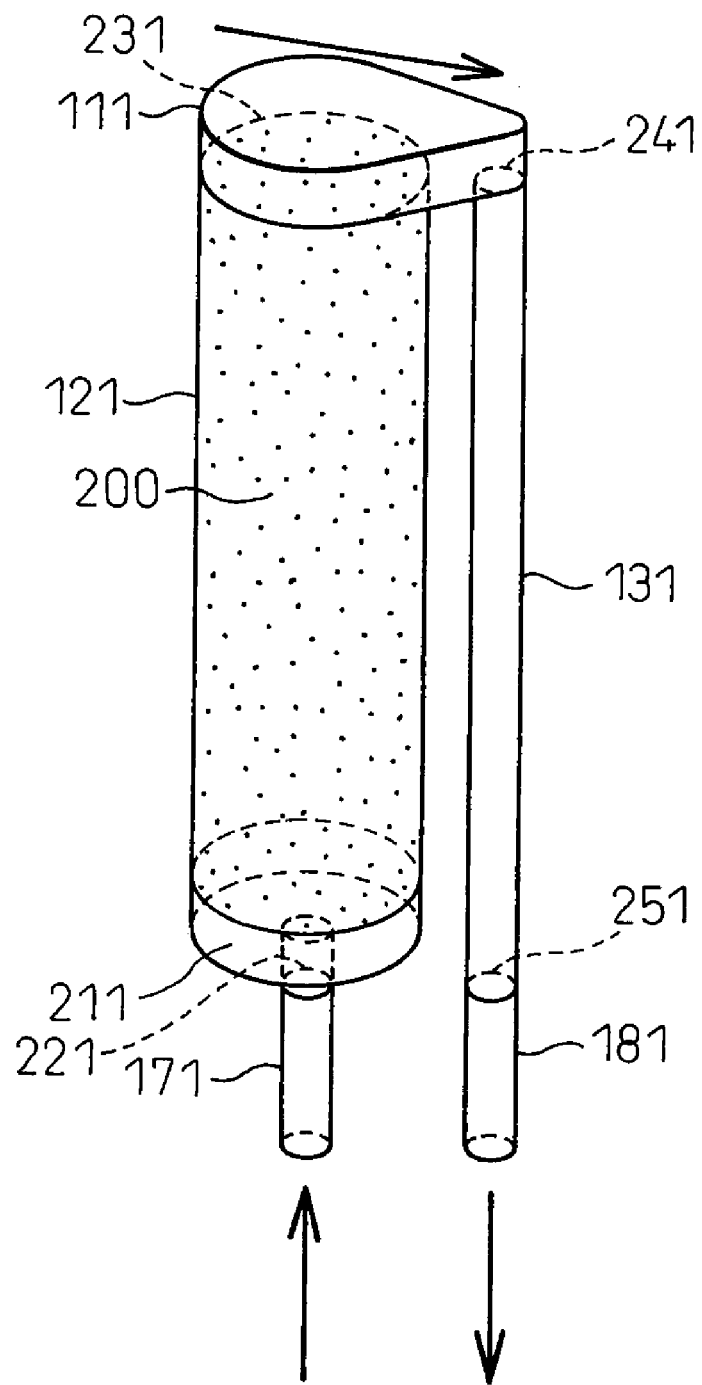
FIG. 8 is a diagram showing a path through which urine is filtered.

FIG. 8 is a diagram showing a path through which urine is filtered.

In FIG. 8, the urine is fed to the filter container 121 in the cassette 110, but the same applies for any one of the other nine filter containers 122 to 130.

The urine transported through the urine inlet tube 171 is introduced into the filter 200 via the inlet port 221 (corresponding to the first inlet port) of the filter container 121, formed in the bottom of the cassette 110, and via the circular lower receiving member 211, and passes through the filter 200 from the bottom toward the top thereof. As the urine passes through the filter 200, components that can interfere with the measurement are removed, as earlier described. The urine exiting through the outlet port 231 (corresponding to the first outlet port) of the filter container 121 is received by the upper receiving member 111 and flows into the discharge drain 131 through the inlet port 241 (corresponding to the second inlet port) thereof. The filtered urine flowing into the discharge drain 131 is discharged outside the cassette section 100 through the outlet port 251 (corresponding to the second outlet port) of the discharge drain, formed in the bottom of the cassette 110, and through the urine outlet tube 181.

The upper receiving member 111 allows the urine passed through the filter 200 to flow into the discharge drain 131, while preventing the resin particles filled as the filter 200 into the filter container 121 from flowing outside the filter container 121. The outlet port 231 of the filter container 121 is formed to have a cross-sectional section larger than that of the inlet port 241 of the discharge drain 131. The upper receiving member 111 has a teardrop shape so as to efficiently cover both the outlet port 231 of the filter container 121 and the inlet port 241 of the discharge drain 131, and is formed from a sintered polyester resin or polyether-based urethane foam or the like. Since the urine flows laterally along the upper receiving member 111 and drops into the discharge drain 131, the flow path is longer than when the urine was made to flow in the direction of the thickness, and thus the teardrop shape is effective in preventing the resins, etc. from flowing outside the cassette holder 121.

The circular lower receiving members 211 to 220 serve to prevent the resin particles filled into the respective filter containers 121 to 130 from flowing outside the filter containers 121 to 130. Further, like the upper receiving members 111 to 120, the lower receiving members 211 to 220 are also formed from a sintered polyester resin or polyether-based urethane foam or the like.

Since the urine inlet ports of the cassette 110, the outlet ports for the filtered urine, and the outlet port for the cleaning liquid 210 are all provided on the underside of the cassette 110, as described above, the cassette 110 can be easily loaded and unloaded. Furthermore, since the urine inlet tubes 171 to 180 and outlet tubes 181 to 190 to and from the cassette holder 160 and the cleaning liquid outlet tube 141 are all provided on the underside of the cassette holder 160, the tubing to the cassette section 100 in the measuring apparatus 1 is simplified in design.

Figure 9:
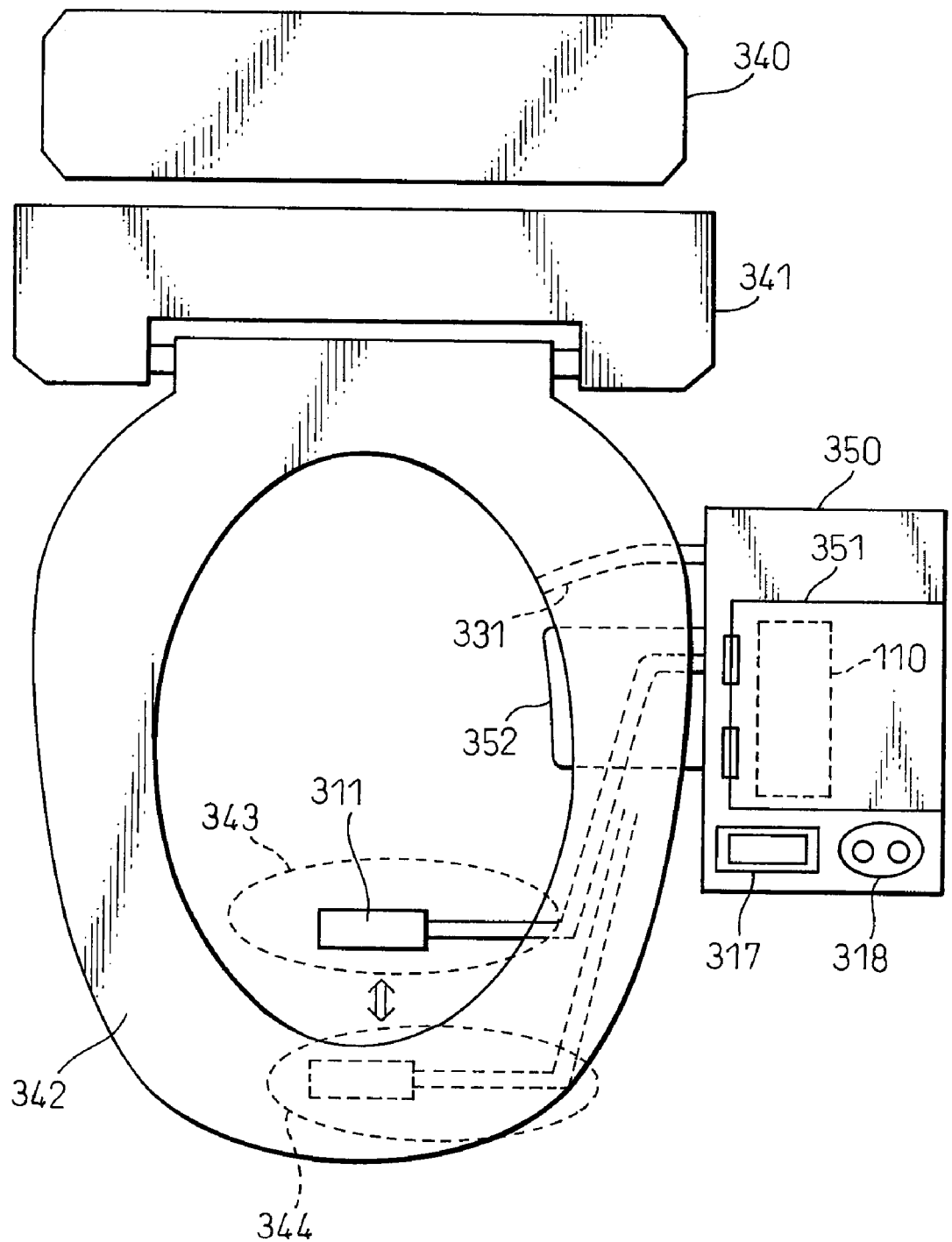
FIG. 9 is a diagram showing an example in which the measuring apparatus shown in FIG. 5 is built into a toilet.
Figure 10:
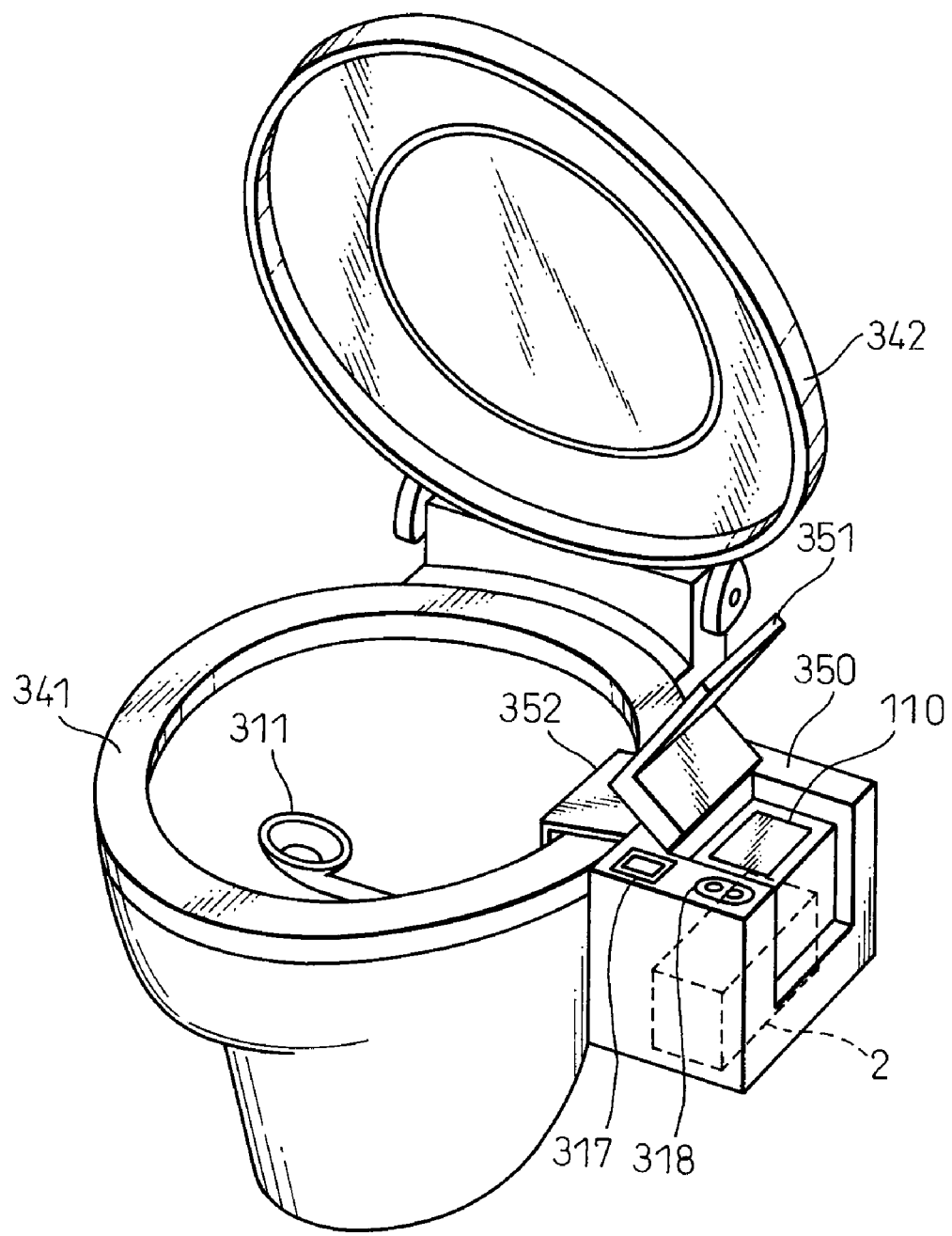
FIG. 10 is a perspective view of the example shown in FIG. 9.

FIG. 9 is a diagram showing an example in which the measuring apparatus 1 shown in FIG. 5 is built into a toilet, and FIG. 10 is a perspective view thereof.

The toilet comprises a water tank 340, a toilet bowl 341, a toilet seat 342, etc. A housing unit 350 is fixed to one side of the toilet bowl 341 by means of a mounting member 352. The measuring apparatus 1, including the optical measuring section 2, but not including the urine collecting section 11, is housed in the housing unit 350. The urine collecting section 11 is movably mounted inside the toilet bowl 341, and is connected to the measuring apparatus 1 housed inside the housing unit 350. A cover 351 is provided on the upper side of the housing unit 350 so that the cassette 110 can be loaded and unloaded from above the housing unit 350 by opening the cover 351. In FIG. 10, the water tank 340 is not shown.

When a measurement start operation is performed on the operation section 318 mounted on the upper surface of the housing unit 350, the urine collecting section 311 is moved from a standby position 344 to a urine collection position 343 by a moving mechanism not shown. The urine collected in the urine collecting section 311 is filtered by the filter 200 and the urine sugar concentration is measured by the optical measuring section 2 under the control of the control section 316, as earlier described. The urine sugar concentration thus measured is displayed on the display section 317. When all the 10 filters 200 in the cassette 110 have been used, the control section 316 displays a warning indication on the display section 317 to indicate that the cassette 110 needs to be replaced.

The specific configuration example of the first embodiment according to the present invention has been described above. In the above embodiment, the cassette 110 has been described as holding 10 filter containers 121 to 130; however, the number of filter containers is not limited to 10, but may be one or any other number. Further, the first and second pumps 312 and 315 may be combined into one unit. The upper lid 101 may be sealed by an adhesive. Further, the cleaning liquid 210 may be a powdered or solid cleaning agent. The material of the cassette need not be limited to any specific material, but use may be made of polypropylene, ABS, polystyrene, acrylic, or the like.

According to the specific configuration example of the first embodiment of the present invention, since the filter for filtering the sample and the cleaning liquid are contained in the same cassette, not only can the cassette or the measuring apparatus be made compact and simple in construction, but the maintenance can be facilitated.

According to the specific configuration example of the first embodiment of the present invention, the cassette loading/unloading mechanism can be simplified as the sample inlet and outlet ports of the cassette and the cleaning liquid outlet port are all provided on the underside of the cassette. Further, the tubing within the measuring apparatus can be simplified in design as the sample inlet and outlet tubes to and from the cassette and the cleaning liquid outlet tube are all provided on the underside of the cassette holder. Furthermore, since the inlet and outlet ports are both provided, the urine sample does not come into contact with the user's hand when unloading the cassette, the design thus being effective in solving hygienic concerns.

Further, according to the specific configuration example of the first embodiment of the present invention, since the outlet port of the filter and the inlet port of the discharge drain are connected by a teardrop-shaped receiving member, the sample can be efficiently transferred from one to the other, while effectively preventing the resin particles from flowing out.

Next, a second embodiment according to the present invention will be described with reference to FIGS. 11 to 13.

Figure 11:
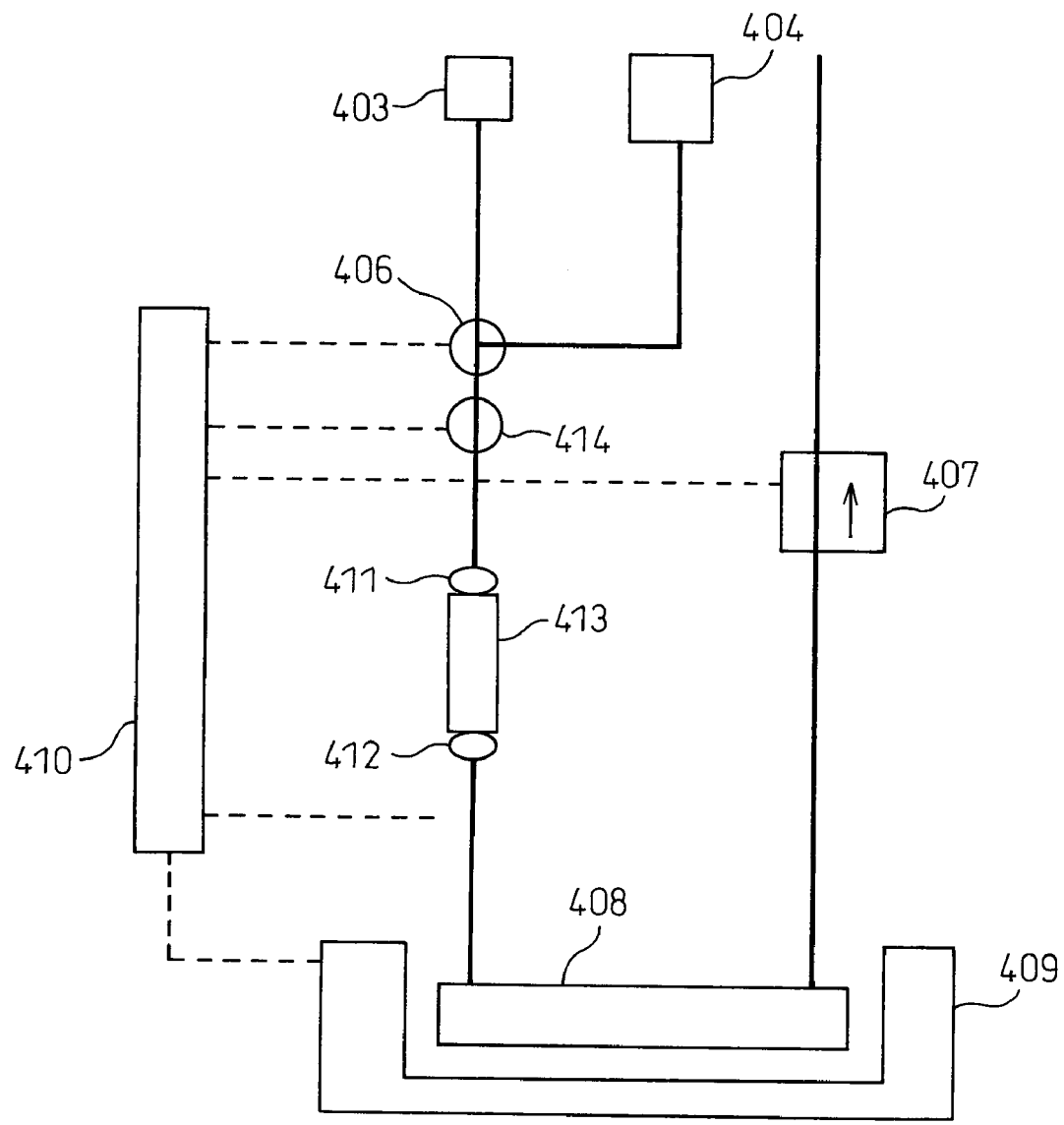
FIG. 11 is a schematic diagram showing the overall system configuration of a measuring apparatus according to a second embodiment.

FIG. 11 is a schematic diagram showing the overall system configuration of a measuring apparatus according to the second embodiment.

A control device 410 comprises a CPU for controlling the entire system, and its peripheral circuitry. An optical measuring device 409 is a device for measuring the angle of optical rotation produced by an analyte solution (urine) held in a measuring cell 408, and performs the measurement under instruction from the control device 410. A cleaning water container 404 is a container for storing a cleaning liquid, and an analyte solution container 403 is a container for holding the analyte solution (urine) to be measured. An electromagnetic valve 406 has the function of connecting to either the cleaning water container 404 or the analyte solution container 403, whichever is selected, under instruction from the control device 410. An electromagnetic valve 414 has the function of opening or closing the passage connecting between the electromagnetic valve 406 and a container 413, under instruction from the control device 410.

Loading/unloading devices 411 and 412 are devices for loading/unloading the container 413 under instruction from the control device 410. The container 413 is formed from polyvinyl chloride, and contains resins (ion-exchange resin and synthetic adsorbent resin) for removing interfering components or contains antiseptics. The container 413 is provided with liquid feed holes at the inlet and outlet sides, and a membrane filter for preventing the passage of resins is provided at the outlet side. A pump 407 delivers the liquid or stops delivering the liquid under instruction from the control device 410.

Next, a changing system for the container 413 will be described in detail.

Figure 12:
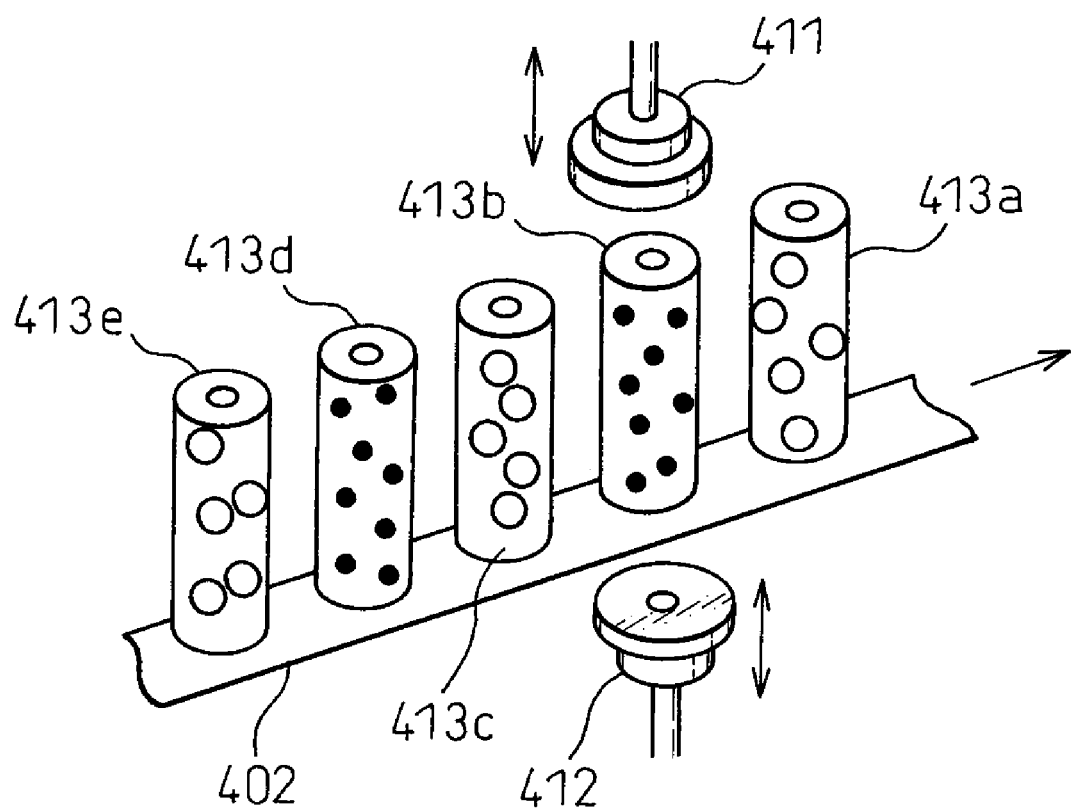
FIG. 12 is a diagram showing the details of an automatic continuous changing mechanism for a container 413.

FIG. 12 is a diagram showing the details of the automatic continuous changing mechanism for the container 413. In the figure, the loading/unloading device 411 moves upward when unloading the container 413 and downward when loading it. On the other hand, the loading/unloading device 412 moves downward when unloading the container 413 and upward when loading it.

When changing the container 413, first the loading/unloading device 411 moves upward and the loading/unloading device 412 downward, and after that, a belt 402 is pulled in the direction shown by arrow in the figure by a prescribed distance until the container 413b comes to the designated position. Then, the loading/unloading device 411 moves downward and the loading/unloading device 412 upward, thus holding the container 413b fixed in position.

With the above operation, the container 413 is automatically changed. Here, the containers 413a, 413c, and 413e contain resins, and the containers 413b and 413d contain antiseptics for cleaning.

In the figure, the container 413a is already used and the container 413b is being positioned for use. That is, after performing the measurement using the container 413a, the process proceeds to the next step to perform cleaning using the container 413b. After that, the process proceeds to perform the measurement using the container 413c, the cleaning using the container 413d, the measurement using the container 413e, and so on. The containers are mounted on the belt 402.

Figure 13:
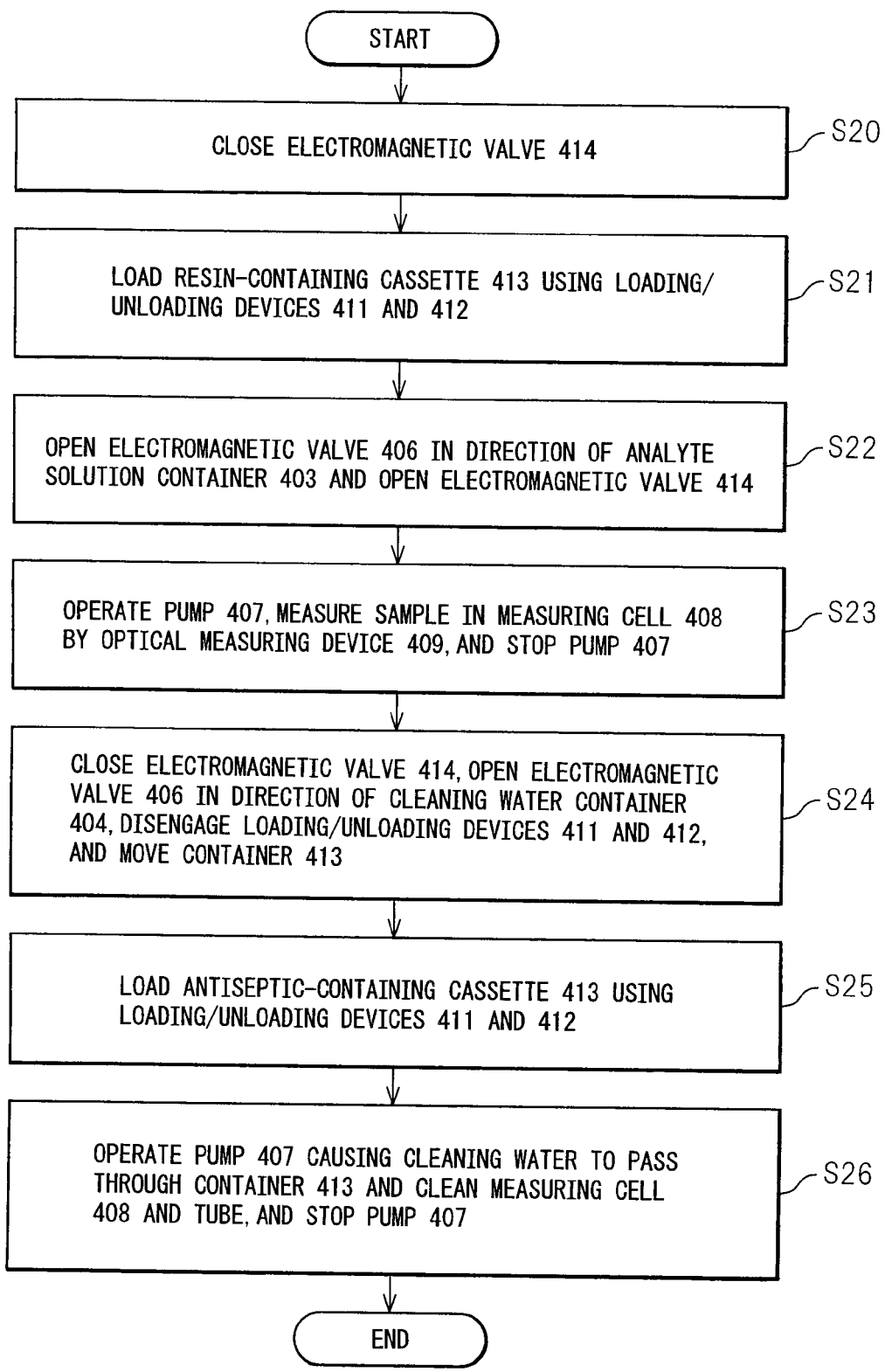
FIG. 13 is a diagram showing a system flowchart of a control device 410 shown in FIG. 11.

FIG. 13 is a diagram showing a system flowchart of the control device 410 shown in FIG. 11.

First, the electromagnetic valve 414 is closed (S20) to stop the solution flow.

Next, the resin-containing container 413 is loaded using the loading/unloading devices 411 and 412 (S21).

Next, the electromagnetic valve 406 is opened in the direction of the analyte solution container 403, and the electromagnetic valve 414 is also opened, thus securing a path for feeding the analyte solution (urine) to the container 413 (S22).

Next, the pump 40 is operated to feed the analyte solution (urine) through the container 413 into the measuring cell 408 for measurement by the optical measuring device 409; after the measurement is done, the pump 407 is stopped and the container 413 is moved (S23).

Next, the electromagnetic valve 414 is closed, the electromagnetic valve 406 is opened in the direction of the cleaning water container 404, the loading/unloading devices 411 and 412 are disengaged, and the container 413 is moved (S24).

Next, the antiseptic-containing container 413 is loaded using the loading/unloading devices 411 and 412 (S25).

Next, the pump 407 is operated, causing the cleaning water to pass through the container 413 and the measuring cell 408, thus cleaning the entire system (S26). During this process, the antiseptics contained in the cleaning container 413 are dissolved into the cleaning liquid which thus serves to inhibit the growth of fungi. That is, growth of fungi can be prevented without having to use a special cleaning liquid but by using only the cleaning water.

The second embodiment according to the present invention has been described above. In the above embodiment, the resin- and antiseptic-containing containers are arranged so that each resin container is followed by one antiseptic container, but the containers may be arranged so that a plurality of resin containers are followed by one antiseptic container. Further, the substance to be contained in the cleaning container is not limited to antiseptics, but instead, a cleaning agent or a chemical or like substance effective for cleaning may be contained therein.

A third embodiment of the present invention will be described below with reference to FIGS. 14 and 15.

Figure 14:
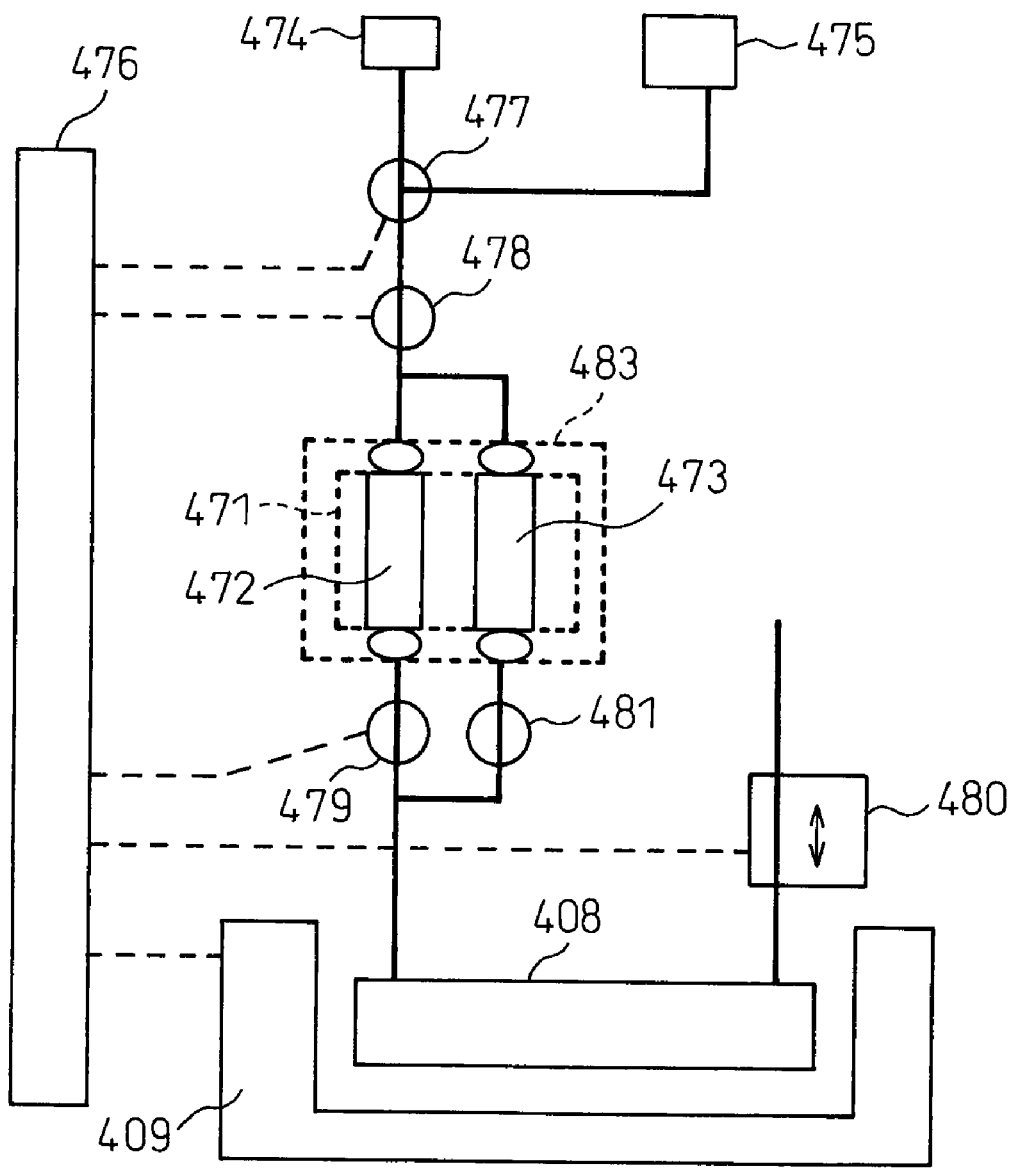
FIG. 14 is a schematic diagram showing the overall system configuration of a measuring apparatus according to a third embodiment.

FIG. 14 is a schematic diagram showing the overall system configuration of a measuring apparatus according to the third embodiment.

In the figure, a control device 476 comprises a CPU for controlling the entire system, and its peripheral circuitry. An optical measuring device 409 is a device for measuring the angle of optical rotation produced by an analyte solution (urine) held in a measuring cell 408, and performs the measurement under instruction from the control device 476. A cleaning water container 475 is a container for storing a cleaning liquid, and an analyte solution container 474 is a container for holding the analyte solution (urine) to be measured. An electromagnetic valve 477 has the function of connecting a cassette 471 to either the cleaning water container 475 or the analyte solution container 474, whichever is selected, under instruction from the control device 476.

The cassette 471 is formed from a plastic material. The cassette 471 accommodates a plurality of container pairs each comprising a container 472 containing a reagent for coloring a first prescribed amino acid and a container 473 containing a reagent for coloring a second prescribed amino acid. An electromagnetic valve 479 has the function of opening or closing the passage connecting between the container 472 and the measuring cell 408, under instruction from the control device 476. An electromagnetic valve 481 has the function of opening or closing the passage connecting between the container 473 and the measuring cell 408, under instruction from the control device 476. A pump 480 has the function of delivering the liquid to the measuring cell 408 or to the opposite side under instruction from the control device 476. The detailed structure of the cassette 471 is the same as that shown in the first embodiment.

Figure 15:
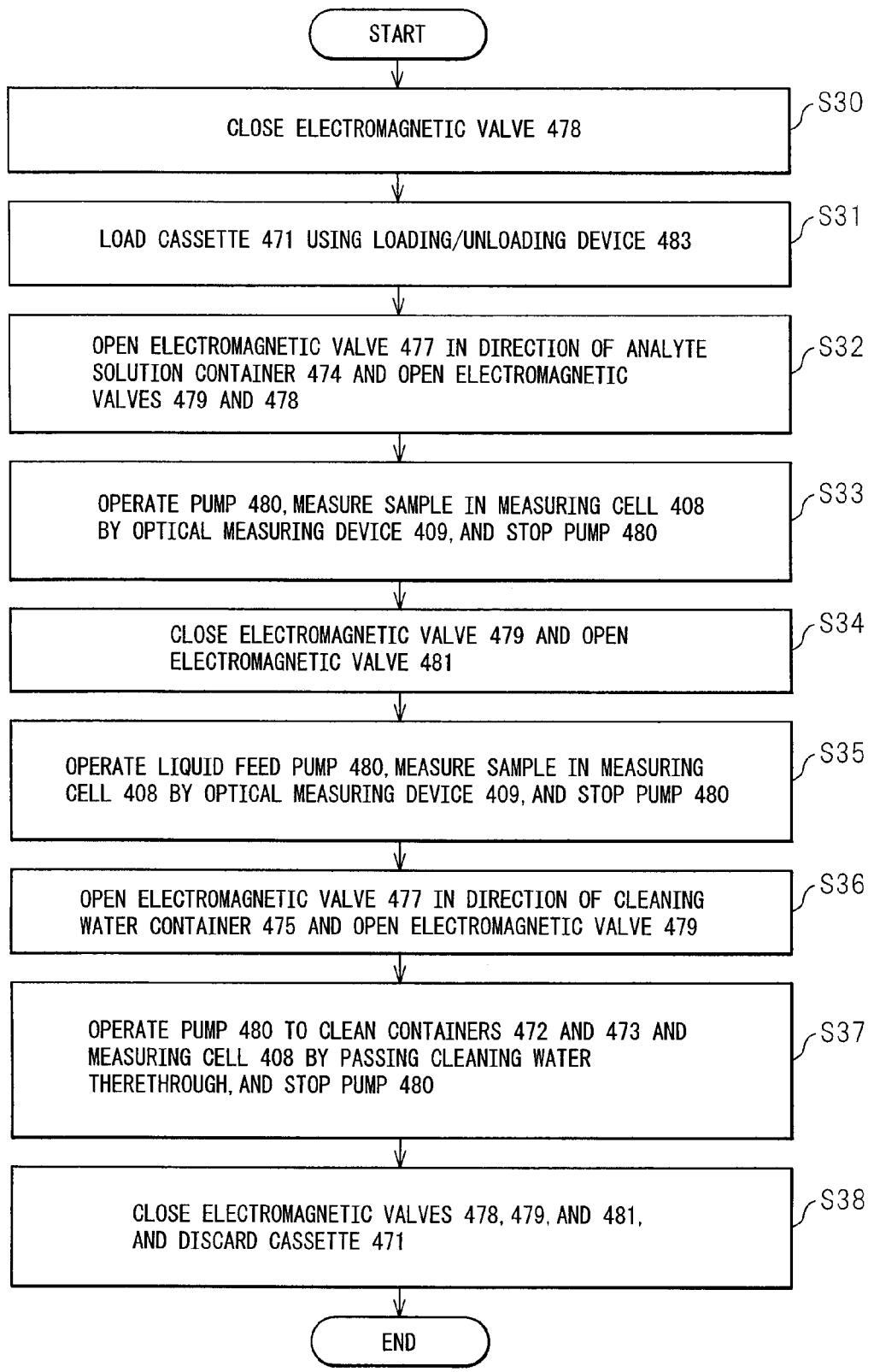
FIG. 15 is a diagram showing a system flowchart of a control device 476 shown in FIG. 14.

FIG. 15 is a diagram showing a system flowchart of the control device 476 shown in FIG. 14.

First, prior to initiating the measurement, the electromagnetic valve 478 is closed to stop the solution flow (S30).

Next, the cassette 471 is loaded using the loading/unloading device 483 (S31).

Next, the electromagnetic valve 477 is opened in the direction of the analyte solution container 474, and the electromagnetic valves 478 and 479 are opened, thus securing a path for feeding the analyte solution (urine) to the container 472 (S32).

Next, the pump 480 is operated in the discard direction, causing the analyte solution (urine) to pass through the container 472 and flow into the measuring cell 408, and the reagent in the container 472 is caused to react with the analyte solution; then, the measurement is made by the optical measuring device 409, and the pump 480 is stopped (S33).

Next, the electromagnetic valve 479 is closed, and the electromagnetic valve 481 is opened, thus securing a path for feeding the analyte solution (urine) to the container 473 (S34).

Next, the pump 480 is operated in the discard direction, causing the analyte solution (urine) to pass through the container 473 and flow into the measuring cell 408, and the reagent in the container 473 is caused to react with the analyte solution, then the measurement is made by the optical measuring device 409, and the pump 480 is stopped (S35).

Next, the electromagnetic valve 477 is opened in the direction of the cleaning water container 475, and the electromagnetic valve 479 is opened in the direction of the measuring cell 408 (S36).

Next, the pump 480 is operated, causing the cleaning water to pass through the containers 472 and 473 and through the measuring cell 408, thus cleaning the entire system, and after the cleaning is done, the pump 480 is stopped (S37).

Finally, the electromagnetic valves 478, 479, and 481 are closed, and the cassette 471 is discarded (S38).

In the foregoing, the first to third embodiments of the present invention have been described as using two containers, but the number of containers is not limited to two, the only requirement being that a plurality of containers be used. Further, the reagents can be changed to match the analyte, and are not limited to those described herein. Further, each cassette may be formed in a cylindrical shape which is easy to fabricate, or in the shape of a polygonal column such as a hexagonal column which can be closely packed in order to save space.

In the first to third embodiments of the present invention, the analyte has been measured using a polarimeter, but alternatively, an optical measuring instrument such as a spectrometer or a biosensor using an enzyme may be used.

In the second embodiment of present invention, the containers 413a, 413c, and 413e contain resins, and the containers 413b and 413d contain antiseptics for cleaning, as shown in FIG. 12. The containers 413 are successively used by moving one container after another to the designated position. That is, when the container 413a is loaded for the measurement of urine sugar, the urine is fed through it, and after that, the container 413b is loaded and the cleaning water is fed to clean the entire system. Since the container 413b contains antiseptics, the measuring apparatus is not only cleaned, but provided with fungus resistance.

Further, in the first embodiment of the present invention, since the resin container 32 containing resins and the cleaning container 30 containing antiseptics are simultaneously loaded, as shown in FIG. 1, cleaning can be done after each cycle of measurement, and the interior of the container 32 can also be cleaned. This structure also makes backwashing possible by flowing the liquid from the outlet side to the inlet side in the direction opposite to the measuring flow direction.

In other words, in the first to third embodiments of the present invention, cleaning agents need not be stored in advance within the apparatus, but a plurality of kinds of containers are loaded and unloaded simultaneously or successively. Since this arrangement serves to save space and maintenance work, and since antiseptics or cleaning agents that match the analyte or the measuring method can be used, optimum and flexible cleaning and measurement can be accomplished.

As described above, according to the first to third embodiments of the present invention, powerful cleaning of the measuring apparatus can be performed using a continuously usable container that uses a cleaning filter containing a cleaning agent or antiseptics for every predetermined number of measurement cycles. Furthermore, by simultaneously connecting a plurality of filters including the cleaning filter, it becomes possible to clean the apparatus without connecting a new filter after each measurement cycle, and in this case, the measuring filter used for the measurement can also be cleaned. Since this structure makes backwashing possible by flowing the liquid from the outlet side to the inlet side in the direction opposite to the measuring flow direction, cleaning is performed by working from the lightly contaminated side toward the heavily contaminated side.

Furthermore, according to the first to third embodiments of the present invention, since reagents are contained in the plurality of filters, a wide variety of analytes can be measured without having to store within the apparatus itself various kinds of reagents that match the various kinds of analytes to be measured and without thus using much storage space within the apparatus.

What is claimed is:

1. A measuring apparatus for filtering a sample, comprising:
    a cassette having a filter for filtering out a measurement interfering component from said sample, a container containing said filter, a cleaning liquid or cleaning agent for cleaning a sample flow channel, and a storage tank for storing said cleaning liquid or cleaning agent;
    a cassette holder for detachably holding said cassette;
    a measuring container for holding said sample from which said measurement interfering component has been filtered out by said filter; and
    an optical measuring section for optically measuring an optically active substance contained in said sample in said measuring container, wherein said container has a first inlet port through which said sample is introduced from outside said cassette, and a first outlet port through which said sample passed through said filter exits, wherein said cassette further includes
- a discharge drain having a second inlet port through which said sample passed through said filter is introduced, and a second outlet port through which said sample introduced through said second inlet port is discharged outside said cassette, and
- a transferring member for transferring said sample exiting from said first outlet port of said container onto said second inlet port of said discharge drain, wherein said storage tank has a third outlet port through which said cleaning liquid or cleaning agent is fed out of said cassette, and wherein said first inlet port, said second outlet port, and said third outlet port are all provided on an underside of said cassette.

2. The measuring apparatus according to claim 1, wherein said filter is formed from resin particles,
said first outlet port is formed to have a larger cross-sectional area than said second inlet port, and
said transferring member is formed in a teardrop shape in order to transfer said sample from said first outlet port to said second inlet port while preventing said resin particles from flowing out.

3. The measuring apparatus according to claim 1, wherein said cleaning liquid or cleaning agent is for cleaning at least said measuring container.

4. A measuring apparatus for filtering a sample, comprising:
- a cassette having a filter for filtering out a measurement interfering component from said sample, a container containing said filter, a cleaning liquid or cleaning agent for cleaning a sample flow channel, and a storage tank for storing said cleaning liquid or cleaning agent;
- a cassette holder for detachably holding said cassette;
- a measuring container for holding said sample from which said measurement interfering component has been filtered out by said filter; and
- an optical measuring section for optically measuring an optically active substance contained in said sample in said measuring container, wherein said container has a first inlet port through which said sample is introduced from outside said cassette, and a first outlet port through which said sample passed through said filter exits, wherein said cassette further includes
- a discharge drain having a second inlet port through which said sample passed through said filter is introduced, and a second outlet port through which said sample introduced through said second inlet port is discharged outside said cassette, and
- a transferring member for transferring said sample exiting from said first outlet port of said container onto said second inlet port of said discharge drain, wherein said storage tank has a third outlet port through which said cleaning liquid or cleaning agent is fed out of said cassette, and wherein said cassette has a plurality of pairs of said filter and said discharge drain.

5. The measuring apparatus according to claim 4, wherein said cleaning liquid or cleaning agent is for cleaning at least said measuring container.

6. A measuring apparatus for filtering a sample, comprising:
- a cassette having a filter for filtering out a measurement interfering component from said sample, a container containing said filter, a cleaning liquid or cleaning agent for cleaning a sample flow channel, and a storage tank for storing said cleaning liquid or cleaning agent;
- a cassette holder for detachably holding said cassette;
- a measuring container for holding said sample from which said measurement interfering component has been filtered out by said filter; and
- an optical measuring section for optically measuring an optically active substance contained in said sample in said measuring container, wherein said container has a first inlet port through which said sample is introduced from outside said cassette, and a first outlet port through which said sample passed through said filter exits, wherein said cassette further includes
- a discharge drain having a second inlet port through which said sample passed through said filter is introduced, and a second outlet port through which said sample introduced through said second inlet port is discharged outside said cassette, and
- a transferring member for transferring said sample exiting from said first outlet port of said container onto said second inlet port of said discharge drain, wherein said storage tank has a third outlet port through which said cleaning liquid or cleaning agent is fed out of said cassette, and wherein said cassette holder has a sample inlet tube for introducing said sample into said first inlet port, a sample outlet tube for discharging said sample from said second outlet port, and a cleaning liquid outlet tube for feeding said cleaning liquid from said third outlet port.

7. The measuring apparatus according to claim 6, wherein said first inlet port, said second outlet port, and said third outlet port are all provided on an underside of said cassette, and
said sample inlet tube, said sample outlet tube, and said cleaning liquid outlet tube are all provided on an underside of said cassette holder.

8. The measuring apparatus according to claim 7, further comprising a feed tube for feeding said filtered sample discharged from said sample outlet tube into said measuring container.

9. The measuring apparatus according to claim 6, wherein said cleaning liquid or cleaning agent is for cleaning at least said measuring container.

10. A measuring apparatus for filtering a sample, comprising:
- a cassette having a plurality of filters for filtering out a measurement interfering component from said sample, a container containing said plurality of filters, a cleaning liquid or cleaning agent for cleaning a sample flow channel, and a storage tank for storing said cleaning liquid or cleaning agent;
- a cassette holder for detachably holding said cassette;
- a measuring container for holding said sample from which said measurement interfering component has been filtered out by one of said plurality of filters;
- an optical measuring section for optically measuring an optically active substance contained in said sample in said measuring container; and
- a controller for selecting one of said plurality of filters so as to filter out said measurement interfering component from said sample.

* * * * *